US008597639B2

(12) United States Patent
Kumagai et al.

(10) Patent No.: US 8,597,639 B2
(45) Date of Patent: Dec. 3, 2013

(54) ADJUNCTIVE AGENT FOR LAVAGING THE ALIMENTARY CANAL COMPRISING BUTYRIC ACID BACTERIUM AND/OR LACTIC ACID BACTERIUM

(75) Inventors: Shinji Kumagai, Sendai (JP); Mamoru Tanaka, Hanishina-gun (JP)

(73) Assignee: Miyarisan Pharmaceutical Co., Ltd. (JP)

( * ) Notice: Subject to any disclaimer, the term of this patent is extended or adjusted under 35 U.S.C. 154(b) by 133 days.

(21) Appl. No.: 13/252,622

(22) Filed: Oct. 4, 2011

(65) Prior Publication Data

US 2012/0027728 A1  Feb. 2, 2012

Related U.S. Application Data

(62) Division of application No. 12/439,406, filed as application No. PCT/JP2007/065779 on Aug. 10, 2007, now abandoned.

(30) Foreign Application Priority Data

Aug. 28, 2006 (JP) .................................. 2006-230810

(51) Int. Cl.
*A01N 63/00* (2006.01)
(52) U.S. Cl.
USPC ...................... 424/93.41; 435/252.7; 435/170
(58) Field of Classification Search
None
See application file for complete search history.

(56) References Cited

U.S. PATENT DOCUMENTS

| 5,077,048 A | 12/1991 | Kimura et al. |
| 5,124,144 A | 6/1992 | Giorgetti et al. |
| 7,026,161 B2 | 4/2006 | Park |
| 2006/0034939 A1 | 2/2006 | Kunogi et al. |

FOREIGN PATENT DOCUMENTS

| EP | 0446069 A1 | 9/1991 |
| FR | 2215952 A1 | 8/1974 |
| JP | 01-125319 A | 5/1989 |
| JP | 01-132527 A | 5/1989 |
| JP | 03-206046 A | 9/1991 |
| JP | 03-284620 A | 12/1991 |
| JP | 05-255097 A | 10/1993 |
| JP | 11-228424 A | 8/1999 |
| JP | 2000-007555 A | 1/2000 |
| JP | 2004-059488 A | 2/2004 |
| WO | 8700754 A1 | 2/1987 |
| WO | 2004004747 A1 | 1/2004 |

OTHER PUBLICATIONS

Limdi et al., World J Gastroenterol Sep. 14, 2006;12(34): 5447-5457.*

Kumagai et al., Progress in Medicine, October issue, vol. 26 No. 10 Oct. 2006.*
Kitajo et al. , Jpn. J. Zootech. Sci., 61 (4) : 344-348, 1990.*
Sanders et al., Invited Review: The scientific basis of *Lactobacillus acidophilus* NCFM functionality as a probiotic, Journal of Dairy Science; vol. 84, pp. 319-331.
Database WPI, Week 200406, Thomas Scientific, London, GB, AN2004-053921.
Database WPI, Week 200409, Thomas Scientific, London, GB, AN2004-091228.
(Anonymous) "Diagnostic and Therapeutic GI Procedures," Merk Manual; vol. 18, pp. 85-86.
[JDDW 2006: Hokkaido] "Studies on the usefulness of butyric acid bacteria preparation in the pretreatment for colonoscopic examination," (Oct. 2006).
[JDDW 2007: Kobe] "Studies on the usefulness of butyric acid bacteria preparation in the pretreatment for colonoscopic examination—2nd Report," (Oct. 2007).
[JDDW 2008: Tokyo] "Studies on the usefulness of butyric acid bacteria preparation in the pretreatment for colonoscopic examination—3rd Report"; (Oct. 2008).
Shinji Kumagai et al., "Studies on the pretreatment method for colonoscopic examination using butyric acid bacteria preparation,"; Progress in medicine, (Oct. 2006), vol. 26, No. 10, pp. 2543-2456.
Mamiko Nagashima et al., "Studies on the pretreatment for colonoscopic examination using oral colonic lavage solution in combination with mosapride citrate," Abstracts of the 60th General Meeting of Japan Gastroenterological Endoscopy Society (Sep. 20, 2000); Gastroentrerol Endosc.; vol. 42, No. 2.
Naoki Wakabayashi et al., "Studies on the effects of itopride hydrochloride administration on the intestinal canal lavage in the pretreatment for conoloscopic examination," Abstracts of the 65th General Meeting of Japan Gastroenterological Endoscopy Society (Apr. 10, 2003); Gastroentrerol Endosc.; vol. 45, No. 1.
Yae Shibuya et al., "Comparison of utility of pretreatment method for colonoscopy by reduced amount of oral intestine cleaning agent," Abstracts of the 32nd General Meeting of Society of Japanese Nursing Research, Adult Nursing I; Abstracts of Society of Japanese nursing research, Adult nursing 1, vol. 32nd (Sep. 25, 2001).
Takahiko Kouda et al., "Studies on the auxiliary cleaning effect of pretreatment for colonoscopic examination using mosapride citrate," Abstracts of the 62nd General Meeting of Japan Gastroenterological Endoscopy Society (Sep. 15, 2001); Gastroenterol Endosc.; vol. 43, No. 2.
Medication Instructions for PURSENNID; Novartis Pharma K.K. (Aug. 2005).
Medication Instructions for LAXOBERON; Teijin Pharma Limited (Apr. 2005).
Biology Dictionary (4th Edition); Iwanami Shoten Publishers (Mar. 21, 1996).

(Continued)

*Primary Examiner* — Irene Marx
(74) *Attorney, Agent, or Firm* — Fox Rothschild LLP; Peter J. Butch, III; Robert N. Henrie, II

(57) ABSTRACT

The present invention provides an adjunctive agent and a method for lavaging the alimentary canal, which is able to reduce a dose of oral cleaning agent for lavaging the alimentary canal and is capable of realizing an excellent cleaning effect at the time of use of the oral cleaning agent. The adjunctive agent comprises butyric acid bacterium (for example, *Clostridium butyricum* and the like) and/or lactic acid bacterium (for example, species belonging to the genus *Lactobacillus* and the genus *Bifidobacterium*).

5 Claims, No Drawings

(56) References Cited

OTHER PUBLICATIONS

Atreja et al., "Making the most of currently available bowel preparations for colonoscopy," Cleveland Clinic Journal of Medicine, (May 2010); vol. 77, No. 5, pp. 317-326.

Madsen, K.L., "The use of porbiotics in gastrointestinal disease," Canadian Journal of Gastroenterogy (Dec. 2001); vol. 15, No. 12, pp. 817-822.

Sanders et al., Invited Review: The scientific basis of *Lactobacillus acidophilus* NCFM functionality as a probiotic, Journal of Dairy Science; vol. 84, pp. 319-331, 2000.

Database WPI, Week 200406, Thomas Scientific, London, GB, AN2004-053921, 2004.

Database WPI, Week 200409, Thomas Scientific, London, GB, AN2004-091228, 2004.

* cited by examiner

ADJUNCTIVE AGENT FOR LAVAGING THE ALIMENTARY CANAL COMPRISING BUTYRIC ACID BACTERIUM AND/OR LACTIC ACID BACTERIUM

CROSS-REFERENCE TO RELATED APPLICATIONS

The present application is a Division of U.S. patent application Ser. No. 12/439,406 filed on Feb. 27, 2009, which in turn is a 35 U.S.C. §371 National Phase application of International Application Serial No. PCT/JP07/65779 filed on Aug. 10, 2007, which claims priority under the Paris Convention to Japanese Patent Application Ser. No. 2006-230810 filed on Aug. 28, 2006. The entire disclosures of all of the above-identified applications are incorporated herein by reference.

TECHNICAL FIELD

The present invention relates to an adjunctive agent for use in lavaging the alimentary canal which is carried out as a pretreatment of alimentary canal radiographic inspection, alimentary canal endoscopy, alimentary canal operation, and the like.

BACKGROUND ART

Conventionally, cleaning agents to be used for lavaging the alimentary canal conducted as a pre-treatment of alimentary canal radiographic inspection, alimentary canal endoscopy, alimentary canal operation, and the like have been known. As to said cleaning agents for lavaging the alimentary canal, for example, those comprising a combination of polyethylene glycol (PEG) and electrolyte (see, for example, JP-A-63-500523, JP-A-I-125319, JP-A-I-132527, JP-A-2-292223 (specification of U.S. Pat. No. 5,124,144)), those comprising a combination of at least one type of water-soluble macromolecule selected from polyethylene glycol, dextran, dextrin, hydroxyethyl starch, polydextrose, gum arabic and pectin and electrolyte (see, for example, JP-A-2-25424 (specification of U.S. Pat. No. 5,077,048) and JP-A-3-206046), and those comprising a combination of erythritol and/or xylitol and electrolyte (see, for example, JP-A-3-284620) have been known.

These conventional cleaning agents for lavaging the alimentary canal are usually required to be taken in an amount of 2-4 L ($2\text{-}4\times10^{-3}$ m$^3$) in the time of its use, and have a drawback of unfavorable taste to be taken in sufficient amount, and further, since patients are forced to have a distress such as nausea after administration, etc. Accordingly, said cleaning agents have problems in common use.

DISCLOSURE OF THE INVENTION

Therefore, an object of the present invention is to provide an adjunctive agent for lavaging the alimentary canal which is capable of reducing a dose of oral cleaning agent for lavaging the alimentary canal, and of realizing excellent cleaning effect without being accompanied by nausea, etc. at the time of use of the oral cleaning agent for lavaging the alimentary canal.

The present inventors have intensively studied to solve the above-described problems, and found that, by taking an adjunctive agent for lavaging the alimentary canal containing butyric acid bacterium and/or lactic acid bacterium before taking an oral cleaning agent for alimentary canal, dosage of the oral cleaning agent for the alimentary canal can be reduced, and at the time of use of said oral cleaning agent for lavaging the alimentary canal, excellent cleaning effects such as reduction of residual substances and air bubbles can be achieved, and have thus completed the present invention.

Thus, the present invention comprises:

(1) An adjunctive agent for lavaging the alimentary canal, comprising butyric acid bacterium and/or lactic acid bacterium.

(2) The adjunctive agent for lavaging the alimentary canal according to the above item (1), wherein said butyric acid bacterium is *Clostridium butyricum*.

(3) The adjunctive agent for lavaging the alimentary canal according to the above item (1), wherein said butyric acid bacterium is at least one species selected from the group consisting of *Clostridium butyricum* MIYAIRI 588 (FERM BP-2789), *Clostridium butyricum* (FERM P-11868), *Clostridium butyricum* (FERM P-11869), and *Clostridium butyricum* (FERM P-11870).

(4) The adjunctive agent for lavaging the alimentary canal according to any one of the above items (1) to (3), wherein said lactic acid bacterium is at least one species selected from the group consisting of lactic acid bacteria belonging to the genus *Lactobacillus* and the genus *Bifidobacterium*.

(5) The adjunctive agent for lavaging the alimentary canal according to any one of the above items (1) to (3), wherein said lactic acid bacterium is at least one species selected from the group consisting of *Lactobacillus acidophilus, Lactobacillus casei, Lactobacillus plantarum, Lactobacillus bulgericus, Bifidobacterium bifidum*, and *Bifidobacterium infantis*.

(6) The adjunctive agent for lavaging the alimentary canal according to any one of the above items (1) to (5), wherein said alimentary canal is the upper alimentary canal and/or the lower alimentary canal.

(7) The cleaning agent for lavaging the alimentary canal according to any one of the above items (1) to (5), wherein said alimentary canal is the large intestine.

(8) A method for lavaging the alimentary canal with the use of an adjunctive agent for lavaging the alimentary canal comprising butyric acid bacterium and/or lactic acid bacterium prior to the use of a cleaning agent for lavaging the alimentary canal.

(9) The method of lavaging the alimentary canal according to the above item (8), wherein said butyric acid bacterium is *Clostridium butyricum*.

(10) The method of lavaging the alimentary canal according to the above item (8), wherein said butyric acid bacteria is at least one species selected from the group consisting of *Clostridium butyricum* MIYAIRI 588 (FERM BP-2789), *Clostridium butyricum* (FERM P-11868), *Clostridium butyricum* (FERM P-11869), and *Clostridium butyricum* (FERM P-11870).

(11) The method of lavaging the alimentary canal according to any one of the above items (8) to (10), wherein said lactic acid bacterium is at least one species selected from the group consisting of lactic acid bacteria belonging to the genus *Lactobacillus* and the genus *Bifidobacterium*.

(12) The method of lavaging the alimentary canal according to any one of the above items (8) to (10), wherein said lactic acid bacteria is at least one species selected from the group consisting of *Lactobacillus acidophilus, Lactobacillus casei, Lactobacillus plantarum, Lactobacillus bulgericus, Bifidobacterium bifidum*, and *Bifidobacterium infantis*.

The method of lavaging the alimentary canal according to any one of the above items (8) to (12), wherein said alimentary canal is the upper alimentary canal and/or the lower alimentary canal.

The method of lavaging the alimentary canal according to any one of the above items (8) to (12), wherein said alimentary canal is the large intestine.

According to the present invention, dose of an oral cleaning agent for lavaging the alimentary canal can be reduced, and excellent cleaning effects such as reduction of residual substances and air bubbles can be achieved without being accompanied by nausea etc. at the time of use of the oral cleaning agent for the alimentary canal.

BEST MODE FOR CARRYING OUT THE INVENTION

Hereinafter, modes for carrying out the present invention are explained in detail.

The adjunctive agent for lavaging the alimentary canal of the present invention comprises butyric acid bacterium and/or lactic acid bacterium, and includes those which comprise at least one species of bacterial cell selected from the group consisting of butyric acid bacterium and lactic acid bacterium together with additives if necessary, to prepare solid preparations such as powders, granules, fine granules or tablets, and the like. In addition, the adjunctive agent for lavaging the alimentary canal of the present invention may be in a form of a dispersion of at least one species of bacterial cell selected from the group consisting of butyric acid bacterium and lactic acid bacterium and other additives if necessary in water or the like filled in a container such as aluminum can, flexible container, and rigid or semi-rigid container, and the like. In this case, the aforementioned dispersion is disinfected or sterilized by a traditional method.

Butyric acid bacteria useful in the present invention include, for example, those belonging to the genus *Clostridium* having no pathogenicity, specifically, the species *Clostridium butyricum* and the like. Specific examples of the aforementioned *Clostridium butyricum* strain include *Clostridium butyricum* MIYAIRI 588 (Accession number: FERM BP-2789), *Clostridium butyricum* (Accession number: FERM P-11868), *Clostridium butyricum* (Accession number: FERM P-11869), *Clostridium butyricum* (Accession number: FERM P-11870), etc. These are all deposited and stored in the NITE Patent Microorganisms Depositary of Institute of Technology and Evaluation. In addition, *Clostridium butyricum* MIYAIRI 588, was deposited on Mar. 6, 1990, at the Fermentation Research Institute, Agency of Industrial Science and Technology, 1-3, Higashi 1-Chrome Tsukuba-shi, Ibarki-ken 3-5, Japan, under the Budapest Treaty on the International Recognition of the Deposit of Microorganisms for the Purposes of Patent Procedure, pursuant to Rule 7.1 of the International Depositary Authority.

Lactic acid bacterium to be used in the present invention include, for example, those belonging to the genus *Lactobacillus* and the genus *Bifidobacterium* having no pathogenicity, and specifically, *Lactobacillus acidophilus, Lactobacillus casei, Lactobacillus plantarum, Lactobacillus bulgericus, Bifidobacterium bifidum, Bifidobacterium infantis*, etc. These are all known lactic acid bacteria, and available in the usual manner.

Method for obtaining large quantity of the bacterial cells of butyric acid bacterium and lactic acid bacterium to be used in the present invention includes a method using the known cultivation technique and the like. For example, in the case of the above-described *Clostridium butyricum* MIYAIRI 588, the bacterial cell can be obtained by the following process: using culture medium comprising carbon source such as cornstarch, powdered sugar, potato starch, soluble starch and glucose; nitrogen source such as meat extract, peptone, casamino acids, solution of amino acids mixture, corn steep liquor and yeast extract; and inorganic salts such as manganese sulfate, ferrous sulfate and calcium carbonate, and using a culture vessel sterilized by autoclaving at 120° C., the seed bacterial cells are inoculated into the culture medium, and cultured at 37° C. for 20-hours. After that, the bacterial cells are harvested by centrifugal separation or the like and dried.

As to the above-described additives, there is no particular limitation as long as they have no adverse effect on the adjunctive agent for lavaging the alimentary canal of the present invention; for example, lactose, cornstarch, microcrystalline cellulose, magnesium stearate, precipitated calcium carbonate, sucrose, trehalose and the like are included.

It should be noted that, unless the purpose of the present invention is impaired, commercially available preparation of butyric acid bacterium may be used. Such preparation of butyric acid bacterium includes, for example, a formulation comprising *Clostridium butyricum* MIYAIRI (product name): MIYA BM® (registered trademark), produced by MIYARISAN Pharmaceutical Co.).

The adjunctive agent for lavaging the alimentary canal of the present invention is to be employed as a cleaning aid for lavaging the alimentary canal using a cleaning agent for the alimentary canal, which is conducted as a pretreatment for X-ray examination, endoscopic examination, surgery of the alimentary canal, and the like, and the aforementioned adjunctive agent for lavaging the alimentary canal is used prior to the use of the above-described cleaning agent for the alimentary canal.

The adjunctive agent for lavaging the alimentary canal of the present invention can be applied to animals which have the gastrointestinal tract, and specifically, to various mammals including human and the like.

The amount of the adjunctive agent for lavaging the alimentary canal of the present invention to be used can be determined appropriately according to the subject to be applied, etc. For example, when applied to a human, a preferable amount to be used is generally in a range of 0.i to 0.3 g/kg, and a range of 0.25 to 0.I g/kg is more preferable. Mode of administration is typically oral administration, but trans-nasal or enema administration is also applicable. As to timing for administration, preferably, administration is performed from 2 days before to the previous day of the alimentary canal lavage. The aforementioned alimentary canal lavage can be performed in the usual manner using known cleaning agent for the alimentary canal (for example, product name NIFLEC® (registered trademark), produced by Ajinomoto Pharma Co., Ltd.).

According to the present invention, by taking an adjunctive agent for lavaging the alimentary canal prior to taking the aforementioned cleaning agent for the alimentary canal, a dosage of the cleaning agent for the alimentary canal can be reduced, and an excellent cleaning effect such as reduction of residual substances and air bubbles can be achieved without being accompanied by nausea etc. at the time of use of the aforementioned cleaning agent for the alimentary canal.

It should be noted that, in the present specification, the upper alimentary canal refers to the esophagus, the stomach and the duodenum, and the lower alimentary canal refers to the small intestine and the large intestine (the vermiform appendix, the ascending colon, the transverse colon, the descending colon, the sigmoid colon, the rectum and the anal canal). Among them, application to the lower alimentary canal is preferable, and application to the large intestine is more preferable.

EXAMPLES

Example 1

Effect of a combined use of the adjunctive agent for lavaging the alimentary canal of the present invention on intestinal canal cleaning in rat.

Rats (Wister, 18-week age, male) were divided into 8 groups with 5 rats in each group, and each group was assigned to a group receiving the adjunctive agent for lavaging the alimentary canal comprising butyric acid bacterium of Clostridium butyricum MIYAIRI (hereinafter, sometimes abbreviated as "butyric acid bacterium group"), a group receiving the adjunctive agent for lavaging the alimentary canal comprising lactic acid bacterium of Lactobacillus acidophilus (hereinafter, sometimes abbreviated as "lactic acid bacterium group"), a group receiving the adjunctive agent for lavaging the alimentary canal comprising lactic acid bacterium of Bifidobacterium bifidum (hereinafter, sometimes abbreviated as "bifidus bacterium group") and a group receiving physiological saline (hereinafter, sometimes abbreviated as "control group").

From 2 days before administration of the cleaning agent for the alimentary canal, solutions comprising $10^8$ cells/cm$^3$ of butyric acid bacterium and each lactic acid bacterium were administered orally to the above-described each group every 2 cm 3 per head twice per day, and the same volume of physiological saline was administered orally to the control group in the same manner. After fasting the rats for 24 hours from the previous day of administration of the cleaning agent for lavaging the alimentary canal, oral cleaning agent for the alimentary canal (product name NIFLEC® (registered trademark), produced by Ajinomoto Pharma Co., Ltd.) was administered into the rats of 4 groups with the dose of 20 cm$^3$/kg and to the other 4 groups with the dose of 10 cm$^3$/kg, and the cleaning of the alimentary canal was carried out by dosing 10 times with an interval of 10 minutes for each cleaning. The rats were slaughtered 60 minutes after the last administration, and the tract from the cecum to short of the anus was immediately stopped using forceps and isolated. Contents were collected separately for the cecum and the large intestine. Each content collected was centrifuged at 6,000 rpm for 15 minutes, and after the precipitate (content residue) was freeze-dried, the mass was determined. The results are shown in the following table I.

TABLE I

THE CONTENT RESIDUE IN EACH GROUP AFTER LAVAGING THE ALIMENTARY CANAL (MEAN VALUE)

| GROUP | Cleaning agent for lavaging the alimentary canal cm$^3$/kg | Content residue (mg) |
| --- | --- | --- |
| Butyric acid bacterium group | 20 | 85 |
| Lactic acid bacterium group | 20 | 90 |
| Bifidus bacterium group | 20 | 91 |
| Control group | 20 | 105 |
| Butyric acid bacterium group | 10 | 103 |
| Lactic acid bacterium group | 10 | 115 |
| Bifidus bacterium group | 10 | 120 |
| Control group | 10 | 128 |

From table 1, it is evident that when 20 cm$^3$/kg of the cleaning agent for lavaging the alimentary canal was used, the mass of content residue was decreased by 15-20% in the groups which used the adjunctive agent for lavaging the alimentary canal, namely, in every group of butyric acid bacterium group, lactic acid bacterium group and bifidus bacterium group, as compared with control group.

Next, it is also evident that when 10 cm$^3$/kg of the cleaning agent for lavaging the alimentary canal was used, the mass of content residue was also decreased in the groups which used the adjunctive agent for lavaging the alimentary canal, namely, in every group of butyric acid bacterium group, lactic acid bacterium group and bifidus bacterium group, as compared with control group. In particular, it is evident that the mass of the content residue in the butyric acid bacterium group was smaller as compared with that in the control group which used 20 cm$^3$/kg of the cleaning agent for lavaging the alimentary canal.

From the above-described results, it is evident that by combined use of the adjunctive agent for lavaging the alimentary canal of the present invention, excellent cleaning effect on the alimentary canal lavage can be obtained, in particular, by the combined use of the adjunctive agent for lavaging the alimentary canal comprising butyric acid bacteria, the amount of the cleaning agent to be used can be reduced significantly.

Example 2

Effect of a combined use of the adjunctive agent for lavaging the alimentary canal of the present invention on intestinal canal cleaning in human.

(1) Test Method

Seventy two (72) subjects aged 20 or over who are going to take endoscopy of the alimentary canal were classified into two groups of those who have defecation every day (Course A) and those who do not have defecation every day (Course B). Subsequently, the subjects were assigned randomly using the envelope method to the following 3 groups: i) a group in which each subject takes 3 g of butyric-acid-bacterium formulation (the formulation comprising Clostridium butyricum MIYAIRI (product name: MIYA BM®, produced by MIYARISAN Pharmaceutical Co. Ltd.) as an adjunctive agent for lavaging the alimentary canal from 2 days before the endoscopic examination for 2 days (a ratio of male to female: 7:3, a ratio of A to B courses: 9:1, and mean age: 54.6 years old, hereinafter, this group is sometimes abbreviated as "two-day group"); 2) a group in which each subject takes 3 g of the above-described butyric-acid-bacterium formulation in the previous day of the endoscopic examination (a ratio of male to female: 8:3, a ratio of A to B courses: 9:2, and mean age:

53.1 years old, hereinafter, this group is sometimes abbreviated as "one-day group"); and 3) a group in which each subject does not take the above-described butyric-acid-bacterium formulation (a ratio of male to female: 28:23, a ratio of A to B courses: 41:10, mean age: 55.1 years old, hereinafter, this group is sometimes abbreviated as "control group").

The subjects belonging to Course A took a laxative of sodium picosulfate on the previous day of the large intestine endoscopy, and took an oral cleaning agent for lavaging the alimentary canal (product name NIFLEC®, 2 L (2×10 produced by Ajinomoto Pharma Co., Ltd.) on the test day. On the other hand, the subjects belonging to Course B took a diet for the large intestine examination, and further took a laxative of sodium picosulfate on the previous day of the large intestine endoscopy, and took an oral cleaning agent for lavaging the alimentary canal (product name NIFLEC®, 2 L ($2\times10^{-3}$ m3), produced by Ajinomoto Pharma Co., Ltd.) on the test day.

(2) Evaluation Method

For the evaluation of the effect on the intestinal canal cleaning, the large intestine was categorized into the rectum, the sigmoid colon, the descending colon, the transverse colon, the ascending colon, and the cecum, and cleaning effect and existence of air bubbles of each site were evaluated using the following criteria based on the results of endoscopic observations.

1. Alimentary canal cleaning effect

Good: 1, washing liquid is almost transparent and good observation is possible by suction.

Common: 2, although a small amount of residual substance is observed, observation can be performed without difficulty by suction, washing or the like.

Bad: 3, presence of residual substance affects observation.

Not acceptable: 4, observation is impossible due to a large amount of residual substances.

2. Presence of gas bubble

Good: 1, gas bubble is hardly observed and good observation is possible.

Common: 2, although gas bubbles are observed slightly, observation can be performed without difficulty.

Bad: 3, gas bubbles are present and affect observation.

Not acceptable: 4, observation is impossible due to presence of many bubbles, and administration of antifoaming agent is required.

(3) Results of the Evaluation

Results of the evaluations (mean value) of cleaning effect and the existence of air bubbles for each site are shown in the following tables 2 and 3, respectively. From these results, in the group which took the adjunctive agent for lavaging the alimentary canal of the present invention, namely, in the two-day group and the one-day group, a significant cleaning effect was confirmed for all sites as compared with the control group which had not taken the aforementioned adjunctive agent for the lavaging the alimentary canal; and in addition, with respect to the presence of air bubbles, reduction of the bubbles was also confirmed for all sites except for the transverse colon and the ascending colon.

TABLE 2

EFFECT OF ALIMENTARY CANAL CLEANING IN EACH GROUP (MEAN VALUE)

| | Two-day group | One-day group | Control group |
|---|---|---|---|
| Rectum | 1.1 | 1.4 | 1.8 |
| Sigmoid colon | 1.2 | 1.6 | 2.0 |
| Descending colon | 1.4 | 1.6 | 2.3 |
| Transverse colon | 1.7 | 1.5 | 2.2 |
| Ascending colon | 1.5 | 1.7 | 2.2 |
| Cecum | 1.5 | 1.5 | 1.9 |

TABLE 3

EXISTENCE OF AIR BUBBLE IN EACH GROUP (MEAN VALUE)

| | Two-day group | One-day group | Control group |
|---|---|---|---|
| Rectum | 1.2 | 1.3 | 1.3 |
| Sigmoid colon | 1.4 | 1.3 | 1.7 |
| Descending colon | 1.6 | 1.1 | 1.8 |
| Transverse colon | 2.0 | 1.3 | 1.8 |
| Ascending colon | 2.0 | 1.2 | 2.1 |
| Cecum | 1.7 | 1.2 | 1.7 |

INDUSTRIAL APPLICABILITY

The adjunctive agent for lavaging the alimentary canal of the present invention is useful as an adjunctive agent to be used for the alimentary canal cleaning which is performed as a pretreatment of alimentary canal radiographic inspection, alimentary canal endoscopy, and alimentary canal operation and the like.

What is claimed is:

1. A method for lavaging the alimentary canal comprising the step of applying to the alimentary canal, an adjunctive agent for lavaging the alimentary canal, said adjunctive agent comprising *Clostridium butyricum* and optionally one or more species selected from the group consisting of lactic acid bacteria belonging to the genus *Lactobacillus* and the genus *Bifidobacterium*, prior to applying to the alimentary canal a cleaning agent for lavaging the alimentary canal.

2. The method of lavaging the alimentary canal according to claim 1, wherein said *Clostridium butyricum* species is *Clostridium butyricum* MIYAIRI 588 (FERM BP-2789).

3. The method of lavaging the alimentary canal according to claim 1, wherein said lactic acid bacterium species is present and comprises at least one species selected from the group consisting of *Lactobacillus acidophilus, Lactobacillus casei, Lactobacillus plantarum, Lactobacillus bulgaricus, Bifidobacterium bifidum*, and *Bifidobacterium infantis*.

4. The method of lavaging the alimentary canal according to claim 1, wherein said adjunctive agent is applied to the upper alimentary canal and/or the lower alimentary canal.

5. The method of lavaging the alimentary canal according to claim 1, wherein said adjunctive agent is applied to the large intestine.

* * * * *